United States Patent [19]
Bright et al.

[11] Patent Number: 4,465,674
[45] Date of Patent: Aug. 14, 1984

[54] AZAHOMOERYTHROMYCIN D DERIVATIVE AND INTERMEDIATES THEREFOR

[75] Inventors: Gene M. Bright, Groton; James R. Hauske, East Lyme, both of Conn.

[73] Assignee: Pfizer Inc., New York, N.Y.

[21] Appl. No.: 529,828

[22] Filed: Sep. 6, 1983

[51] Int. Cl.³ .................. A61K 31/71; C07H 17/08; C12P 19/62
[52] U.S. Cl. .................. 424/180; 424/181; 536/7.2; 536/7.4; 435/76
[58] Field of Search .............. 424/180, 181; 536/7.2, 536/7.4

[56] References Cited

U.S. PATENT DOCUMENTS 3,736,313 5/1973 Jones et al. .................. 536/7.2
4,328,334 5/1982 Kobrehel et al. .................. 536/7.4

FOREIGN PATENT DOCUMENTS 2094293 9/1982 United Kingdom .................. 536/7.4

Primary Examiner—Johnnie R. Brown
Attorney, Agent, or Firm—Charles J. Knuth; Albert E. Frost; Robert K. Blackwood

[57] ABSTRACT

Antibacterial 9-deoxo-9a-methyl-9a-aza-9a-homoerythromycin D, pharmaceutically-acceptable salts thereof, pharmaceutical compositions comprising antibacterially-effective amounts thereof, a method of treatment of bacterial infections with antibacterially effective amounts thereof, and intermediates for the synthesis thereof from erythromycin D.

6 Claims, No Drawings

AZAHOMOERYTHROMYCIN D DERIVATIVE AND INTERMEDIATES THEREFOR

BACKGROUND OF THE INVENTION

The present invention is concerned with antibacterial 9-deoxo-9a-methyl-9a-aza-9a-homoerythromycin D, pharmaceutically-acceptable salts thereof, and intermediates useful in the preparation thereof from erythromycin D and certain of its esters.

Erythromycin D is a known macrolide antibiotic, having the formula (I), was originally isolated

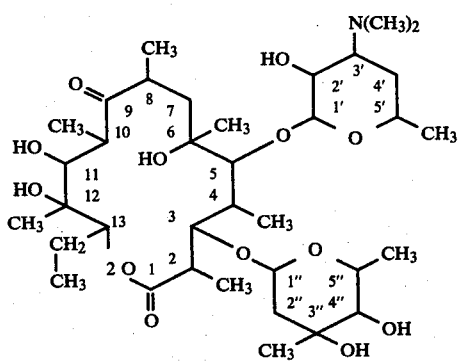

by Majer et al., J. Am. Chem. Soc., 99, pp. 1620–1622, (1977) as a trace component from an industrial erythromycin A purification side stream. More recently, a practical preparation of erythromycin D by direct fermentation has become available. Celmer et al., copending U.S. patent application Ser. No. 367,820, filed Apr. 12, 1982. That fermentation method is also fully disclosed in the Preparation section below.

The present therapeutic compound, which is of the formula (III) below, is structurally related to the previously reported erythromycin A derivative of the formula (III), the subject of British patent application No. 2,094,293, as well as of Bright, copending U.S. patent application Ser. No. 399,401, filed July 19, 1982, now abandoned. In that British application, the compound of the formula (III) is named as the Nmethyl derivative of "11-aza-10-deoxo-10-dihydroerythromycin A", a name coined earlier by Kobrehel et al., U.S. Pat. No. 4,328,334 for the precursor compound of the formula (V). For the latter ring expanded (homo), aza (nitrogen substituted for carbon) erythromycin A derivative, we prefer the name 9-deoxo-9a-aza-9a-homoerythromycin A. That compound could also be named as a 10-aza-14-hexadecanolide derivative.

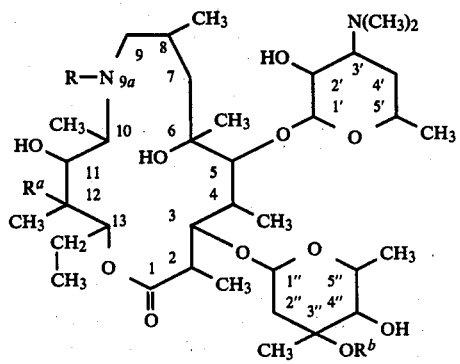

(II) R=methyl, $R^a=R^b=$hydrogen
(III) R=methyl, $R^a=$hydroxy, $R^b=$methyl,
(IV) R=hydrogen, $R^a=R^b=$hydrogen,
(V) R=hydrogen, $R^a=$hydroxy, $R^b=$methyl.

SUMMARY OF THE INVENTION

The present invention encompasses the antibacterial compound 9-deoxo-9a-methyl-9a-aza-9a-homoerythromycin D, having the above formula (II), pharmaceuticallyacceptable salts thereof, pharmaceutical compositions thereof, and a method of use thereof in the treatment of bacterial infections in mammals.

The present therapeutic compound (II) shows a relatively broad spectrum of antibacterial activity which includes erythromycin A and D susceptible organisms and, in addition, many Gram negative microorganisms resistant to erythromycin A and D. The compound (II) is of especial value in the oral treatment of susceptible bacterial infections in mammals.

The present invention also encompasses the valuable intermediate compounds 9-deoxo-9a-aza-9a-homoerythromycin D [having the above formula (IV)], and 9a-aza-9a-homoerythromycin D [also corresponding to the above formula (IV), having a ketone group at the 9-position].

DETAILED DESCRIPTION OF THE INVENTION

The therapeutically valuable compound, 9-deoxo-9a-methyl-9a-aza-homoerythromycin D, of the above formula (II), is readily prepared by a multistep chemical sequence from erythromycin D, of the above formula (I), or its 3",4"-di-O-acetyl, 3"-O-acetyl-4"-O-propionyl, or 4"-O-acetyl esters, all available by the fermantation process of the Celmer et al. application cited above, also described in the Preparation section below.

The first step of the present multistep sequence involves the reaction of erythromycin D or one of its esters with hydroxylamine or a hydroxylamine salt (conveniently the hydrochloride salt) to form the corresponding erythromycin D or ester thereof. Under presently preferred conditions, at least one molar equivalent, usually an excess, e.g., 10-30 equivalents, of the hydroxylamine is employed; in an excess of a weakly basic, tertiary amine (preferably pyridine) as solvent; at a temperature in the range 0°–75° C., conveniently in the range of 20°–60° C.

When the starting material is an ester, the acetyl and/or propionyl groups are conveniently removed at the oxime stage, readily accomplished by the action of excess concentrated NH₄OH in methanol. Temperature is not critical, e.g., 0°-50° C. is generally satisfactory, but ambient temperatures are most convenient.

The resulting erythromycin D oxime is rearranged to the 9a-aza-9a-homoerythromycin D via a Beckman rearrangement. The preferred conditions employ an excess (e.g., 2-4 molar equivalents) of an organic sulfonyl chloride, preferably p-toluenesulfonyl chloride, which is reacted with the oxime (as free base or as an acid salt) in a mixture of a lower ketone (e.g., methyl ethyl ketone, acetone) and water containing a large molar excess of sodium bicarbonate, at a temperature of 0°-50° C., preferably at 0°-30° C., conveniently at ambient temperature.

The C-9 amide carbonyl of said 9a-aza-9a-homoerythromycin D is then conveniently reduced to the corresponding dihydro derivative, i.e., 9-deoxo-9a-aza-9a-homoerythromycin D, of the above formula (IV), by reduction with sodium borohydride (preferably in excess to force the reaction to completion in a reasonable time period, but with at least two equivalents). The reduction is carried out in a suitable protic solvent, such as a lower alkanol (preferably methanol) at 0°-50°, conveniently at ambient temperature.

Final methylation of (IV) to yield the compound (II) is accomplished by reductive methylation, using formaldehyde in the presence of a reducing agent, such as hydrogen and a noble metal catalyst, sodium cyanoborhydride, or, preferably, formic acid. The reaction is preferably carried out with at least one equivalent (most preferably about 2 equivalents) each of formaldehyde and formic acid in a reaction-inert solvent at 20°-100° C.; most preferably 40°-70° C. The preferred solvent is chloroform. As used herein, the expression "reaction-inert solvent" refers to any solvent which does not interact with reagents or products in a manner which adversely affects the yield of the desired product.

Since compound (II) of the present invention contains two basic nitrogen atoms, pharmaceutically acceptable mono and di acid addition salts are formed by contacting the free base (II), respectively, with substantially one equivalent of the acid or with at least two equivalents of the acid. Salts are generally formed by combining the reagents in a reaction inert solvent; if the salt does not precipitate directly, it is isolated by concentration and/or addition of a nonsolvent. Suitable pharmaceutically acceptable acid addition salts include, but are not restricted to those with HCl, HBr, HNO$_3$, H$_2$SO$_4$, HO$_2$CCH$_2$CH$_2$CO$_2$H, cis- and trans-HO$_2$CCHCHCO$_2$H, CH$_3$SO$_3$H and p-CH$_3$C$_6$H$_4$SO$_3$H.

The antibacterial activity of the compound of the formula (II) is demonstrated by measuring its minimum inhibitory concentrations (MIC's) in mcg./ml. against a variety of microorganisms in brain heart infusion (BHI) broth. Generally twelve 2 fold dilutions of the test compound are employed, with initial concentration of the test drug being in the range of 50 to 200 mcg./ml.

TABLE I

| | | In vitro Activity of Compound (II) and Related Compounds | | | |
|---|---|---|---|---|---|
| | | MIC Values (micrograms/ml.) | | | |
| | | (1) | (2) | (3) | (4) |
| Staph. aur. | 005 | 0.05 | 0.39 | 0.20 | 0.39 |
| | 052 | 0.10 | 0.39 | 0.39 | 0.78 |
| | 400 | 6.25 | 6.25 | 25 | (a) |
| Staph. epi | 111 | 0.05 | 0.20 | 0.10 | 0.39 |
| Strep. faec. | 006 | 0.39 | 0.39 | 1.56 | 3.12 |
| Strep. pyog. | 203 | 0.025 | 0.025 | 0.025 | 0.025 |
| E. Coli | 125 | (a) | (a) | 12.5 | 25 |

TABLE I-continued

| | | In vitro Activity of Compound (II) and Related Compounds | | | |
|---|---|---|---|---|---|
| | | MIC Values (micrograms/ml.) | | | |
| | | (1) | (2) | (3) | (4) |
| | 129 | (a) | (a) | 6.25 | 12.5 |
| | 266 | (a) | (a) | 6.25 | 12.5 |
| | 470 | 1.56 | 3.12 | 0.78 | 0.39 |
| Kleb. pn. | 009 | (a) | (a) | 12.5 | 50 |
| | 031 | (a) | (a) | 12.5 | 50 |
| Kleb. oxy. | 024 | (a) | (a) | 25 | 50 |
| Past. mult. | 001 | 0.78 | 6.25 | 0.10 | 0.20 |
| Serr. mar. | 017 | (a) | (a) | 50 | (a) |
| Neiss. sic. | 000 | 3.12 | 6.25 | 0.39 | 0.78 |
| Ent. aerog. | 040 | (a) | (a) | 12.5 | 50 |
| Ent. cloac. | 009 | (a) | (a) | 25 | (a) |
| Prov. strua. | 013 | (a) | (a) | 50 | (a) |
| H. influ. | 012 | 3.12 | 25 | — | 3.12 |
| | 036 | 3.12 | 50 | 0.78 | 3.12 |
| | 038 | 1.56 | 25 | 0.78 | 1.56 |
| | 042 | 3.12 | 25 | 0.78 | 3.12 |
| | 051 | 3.12 | 12.5 | 1.56 | 3.12 |
| | 073 | 3.12 | 50 | 0.78 | 0.39 |
| | 078 | 1.56 | 12.5 | 0.39 | 0.78 |
| | 081 | 3.12 | 25 | 0.78 | 3.12 |

(a) greater than 50
(1) Erythromycin A
(2) Erythromycin D
(3) 9-Deoxo-9a-methyl-9a-aza-9a-homoerythromycin A
(4) 9-Deoxo-9a-methyl-9a-aza-9a-homoerythromycin D The susceptibility (MIC) of the test organism is accepted as the lowest concentration of compound capable of producing complete inhibition of growth as judged by the naked eye. A same day comparison of the activity of 9-deoxo-9a-methyl-9a-aza-9a-homoerythromycin D (II) with that of erythromycin D, erythromycin A and 9-deoxo-9a-methyl-9a-aza-9a-homoerythromycin A controls is shown in Table I.

Additionally, compound (II) is tested in vivo by the well-known mouse protection test, or by a micro-biological (bioassay) determination of serum levels in a variety of mammals (e.g., mouse, rat, dog). Using mice as the test species, compound (II) has been shown to be exceptionally well absorbed after oral dosage, providing exceptionally high and long lasting serum levels.

For the treatment of systemic infections in animals, including man, caused by susceptible microorganisms, compound (II) is dosed at a level of 2.5-100 mg./kg. per day, preferably 5-50 mg./kg./day, in divided doses, or preferably by a single daily dose. Variation in dosage will be made depending upon the individual and upon the susceptibility of the microorganism. These compounds are dosed orally or parenterally, the preferred route being oral. The susceptibility of microorganisms isolated in the clinics is routinely tested in clinical laboratories by the well-known disc-plate method. Compound (II) is generally the compound of choice when it shows a relatively large zone of inhibition against the bacteria causing the infection to be treated.

Preparation of optimal dosage forms will be by methods well known in the pharmaceutical art. For oral administration, the compounds are formulated alone or in combination with pharmaceutical carriers such as inert solid diluents, aqueous solutions or various nontoxic organic solvents in such dosage forms as gelatin capsules, tablets, powders, lozenges, syrups and the like. Such carriers include water, ethanol, benzyl alcohol; glycerin, propylene glycol, vegetable oils, lactose, starches, talc, gelatins, gums and other well known carriers. The parenteral dosage forms required for the above systemic use are dissolved or suspended in a pharmaceutically-acceptable carrier such as water, saline, sesame oil and the like. Agents which improve the suspendability and dispersion qualities can also be added.

For the topical treatment of superficial infections in animals, including man, caused by susceptible microorganisms, the compound (II) is formulated by methods well known in the pharmacist's art into lotions, ointments, creams, salves, gels, or the like at concentrations in the range 5-200 mg./cc. of the dosage form, preferably in the range 10-100 mg./cc. The dosage form is applied at the site of infection ad libitum, generally at least once a day.

The present invention is illustrated by the following examples. However, it should be understood that the invention is not limited to the specific details of these examples.

EXAMPLE 1

3'',4''-Di-O-acetylerythromycin D Oxime

3'',4''-Di-O-acetylerythromycin D (2.0 g., 2.54 mmoles) and hydroxylamine hydrochloride (3.17 g., 45.7 mmoles) were combined in 55 ml. of pyridine and stirred 24 hours at 55° C. The reaction was poured into a mixture of $H_2O$ and $CH_2Cl_2$. The aqueous phase was separated and extracted with fresh $CH_2Cl_2$. The organic layers were combined with an equal volume of fresh $H_2O$ and the pH adjusted to 10.0 with dilute NaOH. The basic aqueous layer was separated and extracted with fresh $CH_2Cl_2$. The organic layers were combined, dried over $Na_2SO_4$ and evaporated to yield title product as a foam, 1.94 g.

$C^{13}$ nmr ($CDCl_3$) 175.6, 170.3, 170.0, 103.6, 98.1, 84.0, 83.5, 77.8, 75.1, 70.9, 68.8, 65.5, 62.8, 44.7, 40.2, 40.0, 38.7, 32.8, 29.7, 27.2, 25.7, 25.3, 23.0, 22.5, 21.5, 20.7, 19.0, 18.3, 11.8, 10.5, 9.6, 9.2.

EXAMPLE 2

Erythromycin D Oxime

Method A

Erythromycin D (200 mg., 0.284 mmole), hydroxylamine hydrochloride (296 mg., 4.26 mmole) and 5 ml. of pyridine were combined and heated at 70° for 4 hours. The reaction mixture was poured into a strired mixture of 20 ml. saturated NaCl, 10 ml. $H_2O$ and 30 ml. $CH_2Cl_2$ and title product further recovered according to the preceding Example as a white foam, 171 mg.

$C^{13}$ nmr ($CDCl_3$) 174.7, 169.6, 104.7, 98.5, 85.5, 83.9, 76.5, 76.3, 75.4, 75.2, 70.8, 70.3, 69.3, 69.1, 65.4, 65.3, 44.5, 40.5, 40.1, 39.7, 39.6, 38.6, 37.4, 32.4, 28.7, 26.8, 25.5, 25.2, 25.1, 21.3, 21.1, 18.8, 18.4, 15.9, 11.8, 10.4, 9.2, 8.9.

Method B

Title product of Example 1 (1.91 g.) was combined with a mixture of 50 ml. each of methanol and conc. $NH_4OH$ and stirred 16 hours at ambient temperature. The reaction mixture was poured into 200 ml. saturated NaCl, 200 ml. $H_2O$ and 300 ml. $CH_2Cl_2$ and title product further recovered as a foam according to the preceding Example, 1.67 g., identical with the product of Method A.

EXAMPLE 3

(A) 9a-Aza-9a-homoerythromycin D

To a stirred solution of the title product of the preceding Example (1.84 g., 2.56 mmoles) in 180 ml. acetone was added 1.18 g. $NaHCO_3$ (14 mmoles), followed by 60 ml. $H_2O$. p-Toluenesulfonyl chloride (976 mg., 5.12 mmoles) was added and the mixture stirred for 2 hours, then poured into 1:1 saturated $NaCl:H_2O$ and $CH_2Cl_2$ in equal volumes. When the pH was below 9.5 it was adjusted to that pH with dil. NaOH. The aqueous layer was separated and extracted with fresh $CH_2Cl_2$. The organic layers were combined, dried and evaporated to yield crude title (A) product (2.24 g., greater than theory).

(B) 9-Deoxo-9a-aza-9a-homoerythromycin D

The entire batch of crude the preceding title (A) product (2.24 g., assumed to be 2.56 mmoles) was dissolved in 50 ml. methanol. $NaBH_4$ (920 mg., 24.3 mmoles) was added portionwise over 4 minutes, with vigorous gas evolution noted. After stirring 45 minutes, the reaction mixture was stripped to a volume of 10 ml. and the resulting suspension poured into 150 ml. 2:1 saturated $NaCl:H_2O$ and 75 ml. $CH_2Cl_2$ and crude product isolated as a foam according to preceding Examples. The crude product was distributed between 30 ml. each of $H_2O$ and $CH_2Cl_2$ and the pH adjusted to 5.1 with dil. HCl. The aqueous was separated and extracted with fresh $CH_2Cl_2$. The aqueous was readjusted to 6.1 with dil. NaOH and extracted 1×30 ml. fresh $CH_2Cl_2$. Finally the aqueous phase was adjusted to 9.5 and product extracted into 2×30 ml. fresh $CH_2Cl_2$. The pH 9.5 extracts were combined, dried and stripped to yield title (B) product as a white foam, 761 mg.

$C^{13}$ nmr ($CDCl_3$) 177.8, 104.5, 97.5, 84.6, 81.0, 76.5, 75.7, 74.1, 73.4, 70.7, 70.6, 69.7, 69.3, 69.2, 66.1, 65.4, 57.0, 56.3, 45.0, 42.9, 41.6, 40.5, 40.2, 38.1, 30.3, 28.5, 27.6, 25.6, 24.6, 22.8, 22.0, 21.3, 18.1, 15.0, 12.8, 10.3, 9.4, 9.1.

EXAMPLE 4

9-Denoxo-9a-methyl-9a-aza-9a-homoerythromycin D

Title product of the preceding Example (760 mg., 1.08 mmoles) was combined with 37% HCHO (0.162 ml., 2.16 mmoles) and $HCO_2H$ (0.075 ml., 2.05 mmoles) in 35 ml. $CHCl_3$ and stirred at 50°–55° for 6 hours. The mixture was then poured into 30 ml. 2:1 saturated $NaCl:H_2O$ and the pH adjusted to 9.5 with dil. NaOH. The aqueous layer was separated and extracted with fresh $CHCl_3$. The organic layers were combined, dried and stripped to yield title product as a white foam, 732 mg.

$C^{13}$ nmr ($CDCl_3$) 178.0, 104.4, 97.1, 84.2, 80.2, 76.4, 75.6, 74.6, 74.1, 70.8, 69.7, 69.6, 69.3, 66.2, 65.5, 62.2, 44.9, 43.1, 41.7, 40.5, 40.2, 38.4, 37.0, 28.5, 27.9, 27.0, 25.6, 24.7, 22.1, 21.3, 18.1, 14.6, 10.2, 9.5, 9.3, 7.6.

The culture below capable of producing the antibiotic complex of erythromycin D and its esters used as starting materials in the present invention is designated Norcardia sp. and has been deposited in The American Type Culture Collection, Rockville, Md. under the accession number ATCC 39043. The permanency of the deposit of this culture at the American Type Culture Collection at Rockville, Md. and ready accessibility thereto by the public are afforded throughout the effective life of the present patent in the event the patent is granted. Access to the culture is available during pendency of the application under 37 CFR 1.14 and 35 USC 122. All restrictions on the availability to the public of the culture deposited will be irrevocably removed either upon granting of the present patent, or upon grant of co-pending patent application Ser. No. 367,820, filed Apr. 12, 1982, whichever might occur earlier.

This novel culture was derived from a soil sample collected in Gose City, Nara Prefecture, Japan, and identified in the culture collection of Pfizer Inc. as N464-21. Its description and classification were provided by Dr. L. H. Huang. It is gram-positive, partially acid-fast, and has a white aerial mycelium and a not readily fragmented substrate mycelium whose color ranges from colorless, cream, pale yellowish to yellowish. The cell wall analyses of sugars, amino acids and mycolates further establish its assignment to the genus Nocardia.

An inoculum is prepared by plating from a freeze-dried lyophile into ATCC #172 broth and growing for 4 days at 28° C. on a shaker. It is then centrifuged for 20 minutes, washed three times with sterile distilled water and planted on media commonly used for identification of members of the Actinomycetales.

Incubation is made at 28° C. and the reuslts may be read at varying times but most commonly is taken at 14 days. The colors are described in common terminology, but exact colors are determined by comparisons with color chips from the Color Harmony Manual, fourth edition. The methods of whole-cell and sugar analyses are those described in Becker et al., Appl. Microbiol. 12: 421-423, 1964; and in Lechevalier et al., J. Lab. Clin. Med. 71: 934-944, 1968. About 30 grams of autoclaved, wet mycelium were used for mycolate analyses, using the method described by Lechevalier et al. in J. Bacteriol. 105: 313-318, 1971.

The culture was identified as follows:

Yeast Extract-Malt Extract Agar (ISP #2 medium, Difco)—Growth good, dark yellowish (near 2ic), moderately raised, wrinkled, aerial mycelium white; reverse same as surface; no soluble pigment.

Oatmeal Agar (ISP #3 medium, Difco)—Growth poor to moderate, white, thin, smooth, aerial mycelium sparse, white; reverse colorless, no soluble pigment.

Inorganic Salts-Starch Agar (ISP #4 medium, Difco)—No growth.

Glycerol-Asparagine Agar (ISP #5 medium, Difco)—Growth good, yellowish (1½ga, 1½ia, 2ia), moderately raised, wrinkled, aerial mycelium white; reverse yellowish (1½ia); no soluble pigment.

Glucose-Asparagine Agar (Waksman, "The Actinomycetes", v. 2, medium #2, p. 328, 1961)—Growth good, white to cream (1½ca), slightly raised, smooth to slightly wrinkled, aerial mycelium white; reverse pale yellowish (1½ea); no soluble pigment.

Czapek-Sucrose Agar (Ibid., medium #1, p. 328)— Growth poor to moderate, white, thin, smooth, aerial mycelium sparse, observed only under the microscope; reverse colorless; no soluble pigment.

Glucose-Yeast Extract Agar (ibid., medium #29, p. 331)—Growth moderate, cream (1½), thin, smooth to slightly roughened, no aerial mycelium; reverse cream; no soluble pigment.

Emerson's Agar (ibid., medium #28, p. 331)— Growth moderate, cream (2ca), thin, smooth to slightly roughened, no aerial mycelium; reverse cream to pale yellowish (2ca, 2 ea); no soluble pigment.

Nutrient Agar (ibid., medium #14, p. 330)—Growth moderate, cream (1½ca), thin to slightly raised, smooth, no aerial mycelium; reverse cream; no soluble pigment.

Bennett's Agar (ibid., medium #30, p. 331)—Growth good, white, cream to pale yellowish (2ca, 2ea), raised, wrinkled, aerial mycelium white; reverse pale yellowish (2ea); no soluble pigment.

Gordon and Smith's Tyrosine Agar (Gordon and Smith, J. Bact., 69: 147-150, 1955)—Growth moderate, cream (1½ca), thin, smooth, aerial mycelium sparse, observed only under the microscope; reverse colorless to cream; no soluble pigment.

Calcium Malate Agar (Waksman, Bact. Rev. 21, 1-29, 1957)—Growth moderate, cream to pale yellowish (1ca, between 1ca and 1ea), thin, smooth, with a few white dots, aerial mycelium white to cream; reverse pale yellowish (1ea); no soluble pigment.

Casein Agar (Gordon and Smith, ibid.)—Growth moderate, white, thin, smooth, aerial mycelium white; reverse colorless; no soluble pigment.

Gelatin Agar (Gordon and Mihm, J. Bact. 73, 15-27, 1957)—Growth moderate, white, thin, smooth, may be slightly wrinkled near the edge, aerial mycelium white; reverse colorless to cream (1½ca); no soluble pigment.

Starch Agar (ibid.)—Growth moderate, white, thin, smooth, or slightly wrinkled near the edge, aerial mycelium white; reverse cream (1½ca); no soluble pigment.

Potato Carrot Agar (Lechevalier, Lab. Clin. Med, 71, 934-944, 1968, but use only 30 g. potatoes, 2.5 g. carrots and 20 g. agar)—Growth moderate, white, thin, smooth, aerial mycelium white; reverse colorless; no soluble pigment.

Tap Water Agar (2%)—Growth scant to poor, white, thin, smooth, submerged, aerial mycelium sparse, observed only under microscope; reverse colorless; no soluble pigment.

Morphological Properties: The fragmentation study was made once every day up to 5 days on glucose-asparagine agar. Fragmentation of the mycelium occurred five days after inoculation. The following morphological observations were made on glucose-asparagine agar after 16-day inoculation; aerial mycelium white, flexuous, wavy or zig-zagged, 0.5-0.9 μm. in diam., may contain swellings and fragments; the swellings terminal, lateral or intercalary, single or contiguous, globose, oval to elliptical, 0.8-1.6 μm. in diam., or 1.2-3×0.7-1.8 μm.; the fragments 1.8-6 (or longer)×0.7-0.9 μm., smooth as revealed by scanning electron microscopy; both the swellings and the fragments often contain refractive oil globules.

Biochemical Properties: Gram-positive; partially acid-fast; melanin production negative; production of hydrogen sulfide negative; nitrate reduction positive; gelatin liquefaction negative; hydrolysis of esculin, hippurate and starch (Gordon et al., Int. J. Syst. Bact., 24, 54-63, 1974) positive; decomposition of adenine, hypoxanthine, and xanthine (ibid.) positive; decomposition of calcium malate, casein, cellulose, tyrosine and urea (ibid.) negative; resistance to lysozyme (ibid.) positive; no growth in Jensen's (Proc. Linn, Soc. N.S.W. 55: 231-248, 1930) or Levine and Schoenlein's (A Compilation of Culture Media, medium 190 2511, 1930) broth; no coagulation and no peptonization on skim milk (Difco).

Utilization of organic acids (Gordon et al., loc. cit.): acetate, malate, propionate and pyruvate utilized; benzoate, citrate, dextrin, lactate, mucate, oxalate, phenol, succinate, and tartrate not utilized.

Acid production from carbohydrates (ibid.): Acid produced from fructose, galactose, glucose, glycerol, inositol, mannitol, mannose, raffinose, ribose, salicin, starch and sucrose; acid not produced from adonitol, arabinose, cellobiose, dulcitol, erythritol, lactose, maltose, melezitose, melibiose, rhamnose, sorbitol, sorbose, trehalose, xylose, and alpha-methyl-d-glycoside.

Carbohydrate utilization (ibid.): Arabinose, fructose, galactose, glucose, glycerol, inositol, maltose, mannitol, mannose, melezitose, raffinose, ribose, salicin, sorbitol, starch, sucrose, trehalose, and xylose utilized; cellobiose, sorbose, and alpha-methyl-d-glycoside doubtfully utilized; adonitol, dulcitol, erythritol, lactose, melibiose, and rhamnose not utilized.

Temperature Relation (ATCC medium #196 in "ATCC Culture Collection Catalog" 14th ed., p. 519, 1980): The culture shows good to excellent growth at 28° C., good growth at 21° C. and 37° C., and no growth at 10° C. and 45° C. It survives at 50° C. for 8 hours.

Cell Wall Analysis: The cell wall contains mesodiaminopimelic acid, arabinose, and galactose.

Mycolate Analysis: The cell wall contains nocardomycolates.

The morphological properties, the nocardomycolic acids, and a type IV cell wall (meso-diaminopimelic acid, arabinose, and galactose) indicate the placement of the present culture in the genus Nocardia. The culture is related to *Nocardia paraffinae* (Jensen) Waksman & Henrici and *N. otitidis-caviarum* Snijders in some morphological and biochemical properties. It differs from *N. paraffinae* in failure to produce acid from maltose, failure to utilize benzoate and succinate, and failure to hydrolyze urea. Five differences distinguish it from *N. otitidis-caviarum:* failure to produce acid from maltose and trehalose, inability to hydrolyze urea, no coagulation on milk, and no growth at 45° C.

To produce the antibiotic complex comprising erythromycin D and its esters (the 3″,4″-diacetate, the 3″-acetate-4″-propionate and the 4″-acetate), the present Nocardia sp. is fermented for three to thirteen days, suitably at 24°–36° C. under submerged conditions with agitation and aeration on media consisting of carbohydrate sources such as sugars, starches, glycerol; organic nitrogen substances such as soybean meal, casamino acids, yeast extract; growth substances such as grain solubles, fish meal, cotton seed meal; mineral salts containing trace elements such as iron, cobalt, copper, zinc, etc. and calcium carbonate or phosphates as buffering agents.

The inoculum required for the fermentation is prepared by scraping vegetative cells from slants or Roux bottles incubated with the Nocardia culture. A solid medium suitable for initial growth on slants and Roux bottles in ATCC medium #172:

|  | gms/liter |
|---|---|
| Glucose | 10 |
| Soluble Starch | 20 |
| Yeast Extract | 5 |
| NZ Amine A | 5 |
| Calcium Carbonate | 1 |
| Distilled Water to 1000 ml; pH to 7.0 with KOH | |
| Add Agar | 20 |

Vegetative cells from slants are used to inoculate either shake flasks or inoculum tanks; or alternately the inoculum tanks are inoculated from shake flasks. In shake flasks growth will generally have reached its maximum in 4 to 6 days whereas in the inoculum tanks growth will usually be at the most favorable period in 3 to 5 days after inoculation. A fermentor can be inoculated with vegetative broth from the inoculum flasks or tank under completely aseptic conditions and fermented for a period of 4 to 6 days. Aeration is maintained in the shake flask by agitation on a shaker or in tanks by forcing sterile air through a sparger at the rate of ½ to 2 volumes of air per volume of broth per minute. The speed of agitation (stirring) depends upon the type of agitator employed; a shake flask is usually run at 150 to 200 cycles per minute and a fermentor at 300 to 1700 revolutions per minute. Sterility is maintained at all times. The temperature is regulated between 26° C. and 34° C. Foaming during the fermentation can be controlled with sterile antifoam such as refined soybean oil, or other suitable antifoam agents in the makeup and as needed aseptically after inoculation.

The fermentation media specified below (with code letter designations of Pfizer Inc.) are as follows:

|  | JD | JL | JLZ-M-1 |
|---|---|---|---|
| Cerelose | 10 g/l. | 10 | 2 |
| Corn starch | 5 | 10 | 10 |
| Corn steep liquor | 5 | — | — |
| Soy flour | — | 10 | 15 |
| Corn fermentable solubles | — | 5 | — |
| Casein | 5 | — | — |
| BYF 300 Yeast | — | — | 5 |
| NZ Amine Ytt | — | 5 | 10 |
| Sodium chloride | — | 2.5 | — |
| Calcium carbonate | 3 | — | 2 |
| Cobalt chloride | 0.002 | 0.01 | 0.01 |
| Potassium phosphate dibasic | — | — | 1 |
| Magnesium sulfate | — | — | 0.5 |
| Acetic acid | — | — | 1.05 (1 ml.) |
| pH | 7.2–7.3 | 7.1–7.2 | — |

|  | JLC-3 | JLC-3' | JLC-6 | JLC-6' |
|---|---|---|---|---|
| Glucose | 20 g/l. | 20 | 20 | 20 |
| NZ Amine-type A | — | 10 | — | 10 |
| Casamino acid | 10 | — | 10 | — |
| Blood meal | 10 | 10 | 10 | 10 |
| DL-Valine | — | — | 5 | 5 |
| DL-Leucine | 10 | 10 | — | — |
| NaCl | 4 | 4 | 4 | 4 |
| CaCO$_3$ | 4 | 4 | 4 | 4 |
| MgCl$_2$ .6H$_2$O | 5 | 5 | 5 | 5 |
| Isoamylalcohol | 0.82 (1 ml.) | 0.82 (1 ml.) | 0.82 (1 ml.) | 0.82 (1 ml.) |
| Phosphate buffer (M/50) | added | added | added | added |

PREPARATION 1

Complex of Erythromycin D and Its Esters

A. Fermentation in 2.5 Liter Pots

Twenty pots were prepared with JL medium, 2.5 liters of medium per pot. One milliliter antifoaming agent was added, and the vessels sealed and sterilized at 120° C. and 15 p.s.i. for 45 minutes. The pots were inoculated with one (2%) or two (4%) inoculum flasks of Nocardia sp. ATCC 39043, fermented for 3 to 6 days at 30° C. (stirred at 1700 revolutions per minute (RPM) and air sparged through the broth at one volume per volume per minute). When fermentation was complete (based on antibiotic disc assay versus *Micrococcus luteus* ATCC 9341 or *B. subtilis* ATCC 6633) the fermentors were stopped, adjusted to pH 8.0 to 9.0 with 50% sodium hydroxide and extracted with ⅓ volume of methylisobutyl ketone. The solvent layer was separated by centrifugation. After sparkling, the antibiotics were back extracted into acid water at pH 3.0, separated and the spent solvent discarded. The acid water was adjusted to pH 8.0 to 9.0, then extracted into ethyl acetate. The solvent was sparkled, dried with anhydrous sodium sulfate and concentrated. The concentrate weighed 2.5 grams.

The concentrate was dissolved in methanol and passed down a column of hydroxypropylated cross-linked dextran gel (Sephadex LH-20, available from Pharmacia Fine Chemicals), with methanol as eluant. The active cuts were combined and concentrated to a syrup, weight approximately 1.7 gms. This concentrate was ready for chromatographing on silica gel to isolate the purified antibiotic complex as detailed in paragraph C below.

The bioactivity of the broth, extracts and column cuts was followed by using a sensitive strain of *Bacillus subtilis* ATCC 6633, *Staphylococcus aureus* ATCC 6538, or *Micrococcus luteus* ATCC 9341. The individual components in the broth, extracts or column cuts were visualized by TLC using Analtech silica gel GF plates in the following systems, chloroform/methanol 9:1 or 3:1 v/v or chloroform/acetone/ammonium hydroxide 25:25:1 v/v/v and spraying the developed plates with vanillin reagent (5 grams vanillin in 100 ml. of ethanol and 50 ml. of 85% phosphoric acid). The plates were heated to 80° C. and the antibiotics were gray to blue/purple on a white background. The individual components were also visualized by overlaying the developed plate with the bacterial organism aforementioned in agar, adding tetrazolium and incubating the plates overnight at 37° C. The antibiotics appeared as clear zones against a reddish background.

B. Large-scale Nocardia sp. ATCC 39043 Fermentation

Scale-up in large fermentors (25 to 1000 gallons) was carried out by preparing large shake flasks containing 0.7 liters of JD or JL medium. The shake flasks inoculum was fermented 3 to 6 days at 28° C., and used to inoculate a 50, 250 or 1500 gallon fementor containing 25, 100 or 1000 gallons of JL or JL2M-1 medium. The fermentors were harvested at 5 to 7 days.

A 1000 gallon fermentation was recovered by extracting the whole broth at pH 9.2 with 200 gallons of methylisobutyl ketone (MIBK). The MIBK extract was separated from the water layer, and back extracted into 25 gallons of acid water, pH 3.4. The acid water was adjusted to pH 9.5, and extracted with 10 gallons of MIBK. The MIBK layer was back extracted into 1 gallon of acid water at pH 2.5 and separated. The acid water was adjusted to 9.5, then extracted with 1 liter of ethyl acetate. The solvent layer was sparkled, then dried with anhydrous sodium sulfate. The ethyl acetate was concentrated to near dryness, yield 18 grams.

The concentrate in methanol was then passed down LH20 Sephadex in methanol and the active cuts combined and concentrated. The yield of concentrate was 12 g., ready for separation of purified antibiotic complex on silica gel.

C. Isolation of Purified Antibiotic Complex

A 50 gallon fermentation of Nocardia sp. ATCC 39043 was extracted with methylisobutyl ketone at a pH of approximately 9.0. Solvent removal left a dark oily residue which was carried through an acid-base work-up as described below. The oil was dissolved in 500 ml. of ethyl acetate (EtOAc) and 500 ml. of water added. The pH was adjusted to 9.0 with dilute NaOH with stirring and the aqueous layer discarded. The EtOAc layer was layered with 500 ml. of water and the pH adjusted with stirring to 3.0 with phosphoric acid. The EtOAc layer was discarded and the acidic aqueous portion layered with 500 ml. of EtOAc and the pH adjusted with stirring to 9.0 with dilute NaOH. The ethyl acetate layer was dried over sodium sulfate and stripped to yield 32.5 grams of red-brown oil. This oil was then chromatographed on 1200 grams of Sephadex LH-20 using methanol as an eluant to produce approximately 16 grams of viscous gum. Chromatography on silica gel utilizing 100% chloroform and increasing amounts of methanol (up to 5% methanol) gave two grams of antibiotic complex.

PREPARATION 2

Erythromycin D

A. Pot Fermentation with In Broth Hydrolysis of Esters

It was observed by TLC analysis that extension of fermentation age increases the proportion of erythromycin D over esters in the broth, accompanied by a rise in pH. Alkaline hydrolysis conditions were then established for the hydrolysis of esters to erythromycin D in broth.

Fermentation was carried out in various media (3 l.) in 6 l. stirred pots at 26° C. for up to 13 days according to the procedure of Example 1. For hydrolysis, 0.5 ml. of whole broth was mixed with 0.5 ml. of saturated aqueous $Ba(OH)_2$. After 15 minutes shaking in a water bath at 30° C., the pH was adjusted to 6.0–8.0 by adding 0.2 ml. of 0.92N HCl. Intact and hydrolyzed broths were assayed for potency using an agar diffusion (plate) assay using *Staph. aureus* 005 with the 3'',4''-diacetate of erythromycin D as standard (i.e. activity is expressed as diacetate equivalents).

The following assays were determined:

| Medium | 7 Days Potency (mcg/ml) | | 8 Days Potency (mcg/ml) | |
|---|---|---|---|---|
| | Intact | Hydrolyzed | Intact | Hydrolyzed |
| JLC-3 | 21.7 | 87.2 | 17.6 | 88.4 |
| JLC-3' | 18.9 | 56.3 | 28.9 | 111.0 |
| JLC-6 | 21.0 | 96.0 | 22.2 | 122.0 |
| JLC-6' | 25.0 | 130.0 | 28.7 | 132.0 |

| Medium | 10 Days Potency (mcg/ml) | | 13 Days Potency (mcg/ml) | |
|---|---|---|---|---|
| | Intact | Hydrolyzed | Intact | Hydrolyzed |
| JLC-3 | 22.2 | 79.2 | 35.3 | 79.2 |
| JLC-3' | 28.7 | 120.0 | 37.8 | 143.0 |
| JLC-6 | 22.2 | 97.5 | 32.9 | 97.5 |
| JLC-6' | 26.9 | 143.0 | 40.7 | 143.0 |

After hydrolysis, the concentrated antibiotic complex, now enriched in erythromycin D, is isolated according to the methods described above. Purified erythromycin D is isolated according to methods detailed below.

B. Hydrolysis of Isolated Antibiotic Complex

Antibiotic complex (16 g.) prepared according to the preceding Preparation was treated with 20 ml. of conc. NH4OH in methanol for 120 hours at room temperature. The reaction mixture was stripped to a foam and redissolved in ethyl acetate. Erythromycin D (5.1 g.) was recovered according to the acid-base extraction work-up procedure of Preparation 1(C).

C. Hydrolysis of 3″,4″-Di-O-acetylerythromycin D

3″,4″-Di-O-acetylerythromycin D (1.91 g.) was combined with 50 ml. conc. NH4OH and 50 ml. methanol for 18 hours. The mixture was poured into a mixture of 200 ml. saturated NaCl, 200 ml. H2O and 300 ml. Ch2Cl2. The aqueous phase was separated and extracted with fresh CH2Cl2. The organic layers were combined, dried over Na2SO4 and evaporated to yield erythromycin D as a foam.

PREPARATION 3

Isolation of Erythromycin D, 3″,4″-Di-O-acetylerythromycin D, 4″-O-Acetylerythromycin D and 3″-O-Acetyl-4″-O-propionylerythromycin D Antibiotic complex (49.05 g.), prepared according to the preceding Examples, was placed on a preparative chromatography column (Jobin-Yvon Chromatospec) packed with 1600 g. silica gel (230-400 mesh) made up in heptane. Fractions of 500 ml. were taken as the solvent was changed to chloroform and then chloroform containing increasing amounts of methanol (up to 20%). The fractions were monitored by TLC, utilizing 1:1 chloroform:methanol as eluant and vanillin spray as described in Example 1. The Rf values of the individual components and yields of crude products by evaporation of appropriately combined fractions were:

|   | Rf | Yield of Crude |
|---|---|---|
| (1) 3″-acetate-4″-propionate | 0.69 | 9.86 g. |
| (2) 3″,4″-diacetate | 0.65 | 8.47 g. |
| (3) 4″-acetate | 0.47 | 24.3 g. |
| (4) erythromycin D | 0.35 | 3.0 g. |

Each of combined fractions (1), (2) and (4) were column chromatographed on 25×1000 mm. columns of silica gel using chloroform containing increasing methanol (up to 5%) to produce analytically pure samples as follows:

|   |   |
|---|---|
| (1) 3″-acetate-4″-propionate | 80 mg. |
| (2) 3″,4″-diacetate | 760 mg. |
| (4) erythromycin D | 1.0 g. |

Combined fractions (3) was rerun on the preparative column to yield 2.19 g. of analytical grade 4″-acetate.

The following physicochemical properties were noted on these products:

3″-O-Acetyl-4″-O-propionylerythromycin D: m.p. 122°-132° C.; no meaningful uv in methanol; ir (KBr) 3500, 2980, 2960, 1470, 1380, 1240, 1180, 1020, 1010, 755 cm$^{-1}$.

3″,4″-di-O-Acetylerythromycin D: m.p. 123°-130° C.; uv (MeOH) 282 nm (max); ir (KBr) 3490, 2980, 2960, 1740, 1460, 1380, 1230, 1180, 1050, 1010 cm$^{-1}$.

4″-O-Acetylerythromycin D: m.p. 124°-130° C.; no meaningful uv in methanol; ir (KBr) 3510, 2980, 2940, 1742, 1460, 1380, 1240, 1180, 1110, 1050, 1010 cm$^{-1}$.

Erythromycin D: identical with previously characterized erythromycin D.

We claim:

1. 9-Deoxo-9a-methyl-9a-aza-9a-homoerythromycin D or the pharmaceutically-acceptable salts thereof.

2. A pharmaceutical composition which comprises an antibacterial amount of the compound of claim 1 and a pharmaceutically-acceptable carrier.

3. A method of treating a bacterial infection in a mammal which comprises administering to said mammal an antibacterially effective amount of the compound of claim 1.

4. A compound selected from the group consisting of 9a-aza-9a-homoerythromcycin D and the 9-deoxo derivative thereof.

5. The compound of claim 4 which is 9a-aza-9a-homoerythromycin D.

6. The compound of claim 4 which is 9-deoxo-9a-aza-9a-homoerythromycin D.

* * * * *